United States Patent
Aunio et al.

(12) 
(10) Patent No.: US 8,465,531 B2
(45) Date of Patent: Jun. 18, 2013

(54) LIGHT THERAPY MODALITY

(75) Inventors: Antti Aunio, Oulu (FI); Juuso Nissilä, Ii (FI)

(73) Assignee: Valkee Oy, Oulunsalo (FI)

(*) Notice: Subject to any disclaimer, the term of this patent is extended or adjusted under 35 U.S.C. 154(b) by 0 days.

(21) Appl. No.: 13/074,230

(22) Filed: Mar. 29, 2011

(65) Prior Publication Data

US 2012/0253427 A1    Oct. 4, 2012

(51) Int. Cl.
*A61N 5/06*    (2006.01)

(52) U.S. Cl.
USPC ............................................. 607/88; 607/89

(58) Field of Classification Search
USPC ........................................ 607/88–90; 351/51
See application file for complete search history.

(56) References Cited

U.S. PATENT DOCUMENTS

| | | | |
|---|---|---|---|
| 5,167,228 A | 12/1992 | Czeisler et al. | |
| 6,350,275 B1 | 2/2002 | Vreman et al. | |
| 7,534,255 B1 | 5/2009 | Streeter et al. | |
| 2005/0137656 A1 | 6/2005 | Malak | |
| 2006/0064144 A1* | 3/2006 | Chen et al. | 607/90 |
| 2007/0167999 A1* | 7/2007 | Breden et al. | 607/88 |
| 2010/0179469 A1* | 7/2010 | Hammond et al. | 604/20 |
| 2011/0313499 A1* | 12/2011 | Smith et al. | 607/113 |

FOREIGN PATENT DOCUMENTS

| | | |
|---|---|---|
| EP | 1074275 | 7/2001 |
| JP | 2009034349 A | 2/2009 |
| WO | 98/51372 A1 | 11/1998 |
| WO | 9851372 | 11/1998 |
| WO | 2006134339 | 12/2006 |
| WO | 2006134339 A1 | 12/2006 |
| WO | 2008/029001 A1 | 3/2008 |
| WO | 2009020862 A2 | 2/2009 |

OTHER PUBLICATIONS

Vaaraniemi, A. "Test: Valkee Bright Light Headset Causes a Burning Feeling", Digitoday, Nov. 24, 2010, pp. 1-4, retrieved from: http://www.digitoday.fi/vimpaimet/2010/11/24/testi-valkeen-kirkasvalokuulokkeetkuumottavat/201016378/66.

Finnish Search Report, dated Nov. 23, 2011, in Application No. 20115295.

* cited by examiner

*Primary Examiner* — Bill Thomson
*Assistant Examiner* — Jeffrey Lipitz
(74) *Attorney, Agent, or Firm* — Tarolli, Sundheim, Covell & Tummino LLP

(57) ABSTRACT

A method of light therapy includes non-invasive, intra-cranial administration of bright light via the ear canal of a subject by using a light intensity of 0.7-12 lumens, and a treatment time of 1-15 minutes. A medical device including radiation elements for directing the light via the ear canal for use in the light therapy is described.

9 Claims, 2 Drawing Sheets

* p-value<0.05 compared with week 0

LIGHT THERAPY MODALITY

FIELD OF THE INVENTION

The present invention relates to light therapy, and especially to light therapy intra-cranially via the ear canal. A medical device for use in the therapy is described.

BACKGROUND OF THE INVENTION

Conventional light therapy comprises exposing a person, and especially the face to bright light, whereby the light is believed to be trans-ported into the brain via the ocular route i.e. through the eyes. The drawback of conventional light therapy is that the amount of light required may be so high that delivering it via the ocular route may cause damage to the eye nerve, headache and other harmful side effects. Another drawback is that the recommended treatment time is at least half an hour, and preferably at least one hour, which limits a person's daily life. The person should also be very close to the light device to realize a therapeutic effect, preferably as close as 10-20 inches (30-50 cm), which makes administration cumbersome. Traditional light therapy lamps also must produce 2,500-10,000 lux, making these light units very high in energy consumption. Late9-11y alternative routes for light therapy have been proposed. However, the knowledge of their effect is very limited and clinical evidence on treatment modalities like dosing or clinical intensities that would be needed for effective treatment have not been studied.

WO98/51372 discloses a method of resetting the circadian clock by applying non-solar photic stimulation of 15 to 150,000 lux, preferably 10,000 to 13,000 lux to any non-ocular region of the human body for 15 minutes to about 12 hours, preferably for 3 hours. Such treatment is hard to carry out without affecting normal activity. A method and device for directing optical radiation energy non-invasively at intra-cranial nerve tissue of a user through an external auditory canal is disclosed in WO2008/029001. The device is suggested for use e.g. in changing diurnal rhythm, in treating jetlag, sleep irregularity, seasonal affective disorder (SAD) etc. No details of treatment modalities are given. Another device for irradiating the inside of the auditory meatus with light is disclosed in JP2009034349.

The mode of action of light therapy is to an extent unknown. This is at least partly due to the fact that there is no easy way to measure the treatment effects induced or the very accurate amount of light delivered to treat a condition or to induce a desired treatment effect. A problem with light therapy is therefore that little is known about the dose of light needed to achieve a therapeutic effect without harmful side effects, as it has been impossible or difficult to administer an accurate dose. Lack of accurate administration has led to varying clinical trial results, and for example FDA being skeptical on approving light therapy devices. Another problem is that little is known about which routes of light treatment are effective. Still another problem is that the knowledge of physiological disorders responsive to light therapy is limited. The present invention provides a solution to overcome or at least alleviate the above problems and drawbacks.

BRIEF DESCRIPTION OF THE INVENTION

The invention provides a new treatment modality for neurological and physiological conditions responsive to bright light. The disclosed treatment modality is a safe, accurately administered, convenient, rapid and effective way of treating these conditions.

The present invention is directed to a method of treating a subject in need of light therapy, said method comprising
providing a medical device comprising radiation means for directing light via the ear canal of the subject,
applying the device to the subject, and
directing non-invasively, intra-cranially via the subject's ear canal bright light having an intensity of 0.7-12 lumens for a treatment time of 1-15 minutes.

The present invention is also directed to a medical device comprising radiation means for directing light via the ear canal of a subject for use in light therapy comprising non-invasive intra-cranial administration of bright light using a light intensity of 0.7-12 lumens for 1-15 minutes.

Specific embodiments of the invention are set forth in the dependent claims. Other objects, details and advantages of the present invention will become apparent from the following drawings, detailed description and examples.

DETAILED DESCRIPTION OF THE INVENTION

Figure 1:
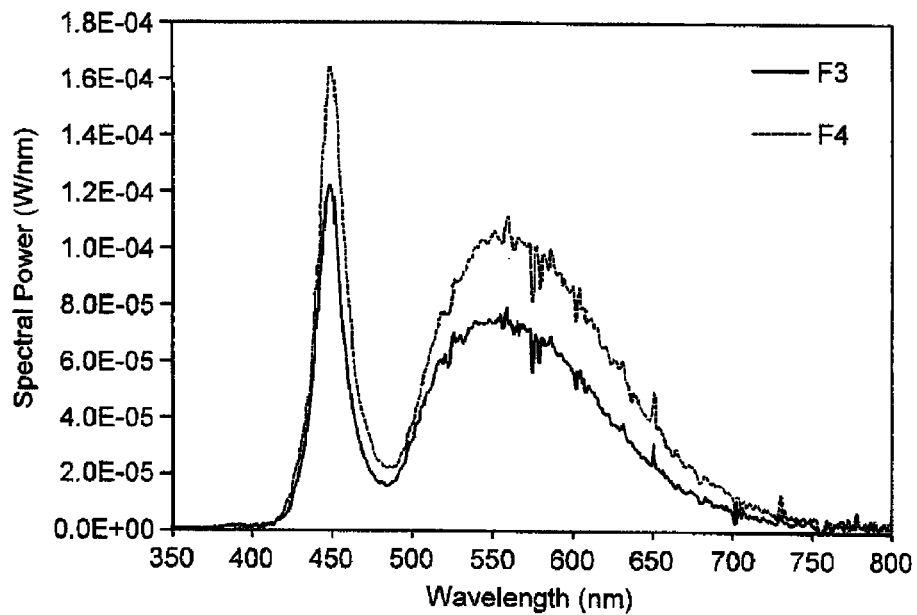
FIG. 1 shows the spectral power distribution of two different led lights F3 and F4.

The invention primarily provides a dose and secondarily a schedule of intra-cranial administration of bright-light direct-to-brain via the ear canal. The subject to be treated is a mammalian, preferably a human being. The bright light is directed non-invasively at the brain tissue through an external auditory canal of the subject to stimulate the subject's brain tissue. Preferably the light is directed via both ear canals. The ear canal enables accurate administration of bright light to induce the intended therapeutic effect without adverse events as the amount of light exposure is highly controlled.

The bright light treatment is conducted using a medical device comprising radiation means for administering the light non-invasively to the brain tissue via the external auditory canal of the subject to be treated. The medical device may be a portable electronic device, wherein the radiation means comprise an optical radiation source for generating optical radiation, and a light guide for guiding optical radiation from the optical radiation source into the external auditory canal. Optical radiation can be directed by means of a plurality of light units such as leds. The device may further comprise adapter means for arranging the radiation means in the user's external ear to enable ease-of-use and accurate administration of light via the ear canal. According to one embodiment, the radiation means and the adapter means form an earpiece to be placed on an earlobe. The adapter means are conveniently arranged so that they at least partly penetrate into the external auditory canal. The device may further comprise a controller to adjust bright light administration and optical radiation, for example intensity, time, spectrum and spatial distribution in the brain. One such device is described in WO2008/29001, which is incorporated herein by reference. Other devices may also be used.

The head 100 area of a user and an example of a portable electronic device comprising radiation means 104A, 104B will be described with reference to FIG. 3.

A portable electronic device is a portable device carried by the user without an external support means. In this case external support refers, for example, to support that, resting on the ground or another fixed structure, supports the device. The user is a person capable of independently using a portable electronic device. The use comprises, for example, placing a portable electronic device on the body, switching the portable electronic device on and off and performing operating settings of the portable electronic device.

In an embodiment, the portable electronic device is user-specific, in which case the person the optical radiation is directed at controls the portable electronic device himself via a user interface, for example.

The radiation member 104A, 104B directs optical radiation 108 at the user's external auditory canal 106A, 106B, which absorbs optical radiation 108 and transmits optical radiation energy 108 to intracranial nerve tissue 102. In that case, the intracranial nerve tissue is subjected to a treatment that has a response in the intracranial nerve tissue. In this context, the terms "optical radiation" and "optical radiation energy" are equivalent concepts, and the same reference number 108 is used to denote both. Optical radiation 108 typically comprises the wavelengths of infrared radiation, visible light and ultraviolet radiation.

Propagation of optical radiation energy 108 is based on the optical propagation of radiation in tissue. When optical radiation energy 108 propagates in tissue, part of it is converted into heat. In addition, the wavelength distribution of optical radiation 108 typically changes due to absorption in tissue.

In the described solution, optical radiation energy 108 is directed at the intracranial nerve tissue 102 non-invasively. In that case, the radiation member 104A, 104B is outside the skin and does not penetrate into the user's tissue. Here also the inner surface of the external auditory canal 106A, 106B is defined as skin. Use of the external auditory canal 106A, 106B as an optical channel and use of the external auditory canal 106A, 106B walls as absorbers of optical radiation 108 enables using low optical power in illuminating the intracranial nerve tissue.

Optical radiation energy 108 is received in the radiation-sensitive intracranial nerve tissue 102, which is stimulated by the optical radiation energy 108. Stimulation typically appears as a nervous and/or hormonal response in the nerve tissue.

The intracranial nerve tissue 102 responsive to optical radiation energy 108 comprises, for example, cerebrum, cerebellum, vestibular organs, auditory organs, organs of smell, bulbus, and/or regions of autonomic regulation. The response may be based on a change in the concentration of melatonin hormone caused by the optical radiation 108, for example.

In an embodiment, the intracranial nerve tissue 102 responsive to optical radiation energy 108 comprises a pineal body, also known as a pineal gland.

In an embodiment, the intracranial nerve tissue 102 responsive to optical radiation 108 comprises a retina, whose ganglia cells may also sense light arriving from behind. Typically, the visual perception of ganglia cells is independent of seeing and not involved therein. Ganglia cells are in particular specialized for diffused light and their photosensitive pigment is melanopsin protein, When subjected to light, ganglia cells signal suprachiasmatic nucleus, which is the primary agent responsible for the diurnal rhythm.

In an embodiment, the intracranial nerve tissue 102 responsive to optical radiation energy 108 comprises a suprachiasmatic nucleus (SON) which regulates the pineal body, which back-regulates the SCN by excreting melatonin.

It should be noted that the above-mentioned intracranial nerve tissues 102 that are responsive to optical radiation energy 108 are only examples. Some of the light also affects through other means, for example through neuroendocrinology of diurnal rhythm. Intracranial nerve tissues, also in the cranial region, have several non-specific responses to optical radiation energy 108 and the temperature increase caused by the optical radiation energy 108. Such responses include increase in the metabolism of tissues and changes in the immune response.

An embodiment of a radiation member 200 will be described with reference to FIG. 4, where radiation member 200 comprises a radiation source (RS) 202. FIG. 4 further illustrates an ear adapter 208 for the radiation member 200 for placing the radiation member 200 at the mouth of the external auditory canal 106A, 106B or on the earlobe 110A, 1108 illustrated in FIG. 3. The ear adapter 208 is, for example, a plug-like structure which is made of plastic or rubber and which may at least partly penetrate into the user's external auditory canal 106A, 106B.

The radiation member 200 may comprise an optically permeable part 210, which allows optical radiation 108 to pass therethrough and forms a structure protecting the radiation source 202. The optically permeable part 210 may also be an opening.

The radiation source 200 is an electro-optical component which converts electric power 206 into optical radiation 108. The radiation source 200 may be, for example, a bulb, light diode, or diode laser. Electric power 206 may be transferred into the radiation member 202 along an electric conductor 204. The radiation member 200 may comprise one or more radiation sources 200, each of which may have a radiation source-specific spectral and/or spatial distribution of optical radiation.

In an embodiment, the spectral distribution of the radiation source 202 may be controlled. In an embodiment, the radiation source comprises RGB (red-green-blue) LEDs, which may together produce a spectrum of optical radiation at a visible wavelength. The spectral distribution of optical radiation may be weighted by controlling or driving each LED separately using a different amount of current. A corresponding LED arrangement may be implemented by infrared LEDs, for instance. The LEDs may be connected in series or in parallel. The connection in series provides the advantage that the same current passes through several LEDs, which provides savings in the total consumption of power as compared to the connection in parallel.

In an embodiment, the radiation source 202 is selected or configured so that the wavelength of the optical radiation 108 is in the area of red color. In that case, the absorption of optical radiation 108 is slight and the amount of optical radiation directed at the intracranial nerve tissue is larger compared to a case where absorption is stronger.

In an embodiment, the radiation source 202 is selected or configured so that the wavelength of the optical radiation 108 is in the infrared area, in which case the effect of the optical radiation energy 108 is directed at target tissues sensitive to thermal radiation, such as the vestibular organ. In this case, the radiation source is an infrared diode, for instance.

In an embodiment, the radiation member 200 comprises sound channels 212A, 212B, which form an air-filled channel between the ear-lobe and the external auditory canal, for instance. The purpose of the sound channel 212A, 212B is to transmit air pressure differences caused by external sounds to the user's eardrum. This allows the user to hear normally as the portable electronic device according to the invention does not function as a hearing protector.

In an embodiment, the radiation member 200 is integrated into a hearing aid, in which case the radiation member 200 comprises a sound source connected to a microphone unit integrated into the radiation member 200 or separate therefrom.

In a preferred embodiment, the portable electronic device is such that at least some of the radiation members 202 or light guides 304 and at least some of the adapter means 208 form an integrated structure. In the following, three different integrated structures will be exemplified.

First, the radiation source 202 and the ear adapter 208 form an integrated structure in FIG. 4. In FIG. 4, the radiation source 202 is substantially inside the ear adapter 208.

Second, an embodiment of a radiation member 300 will be described with reference to FIG. 5 where optical radiation 306 is transmitted to the radiation member 200 along an optical light guide 304. The optical light guide 304 is, for example, an optical fibre. At an end of the optical light guide 304, there may be a lens or the end of the optical light guide 304 may be shaped so as to direct optical radiation 108 at the external auditory canal 106A, 106B in a desired manner. The portable electronic device may comprise several light guides 304, each of which may emit optical radiation 108 at a light guide-specific spectral and/or spatial distribution of the optical radiation 108. In this embodiment, the radiation member 300 may further comprise an ear adapter 208, in which case the ear adapter 208 and the end of the light guide 304 form an integrated structure.

The third way of implementing integration is the most far-going one, i.e. the ear adapter 208 also functions as a light guide or as an end of the light guide, i.e. is capable of transmitting light into the ear. This is achieved for example by using a suitable material in the production of the ear adapter 208. In a way, this third approach is a more advanced version of the second integrated version presented above.

The three examples of integration described above could be generalized by stating that in a preferred embodiment of the portable electronic device, at least some of the radiation means 200, such as the radiation source 202 in FIG. 4, for example, or the end of the light guide 304 in connection with the radiation source, as in FIG. 5, form an integrated structure with the adapter means 208, such as an ear adapter.

Figure 3:
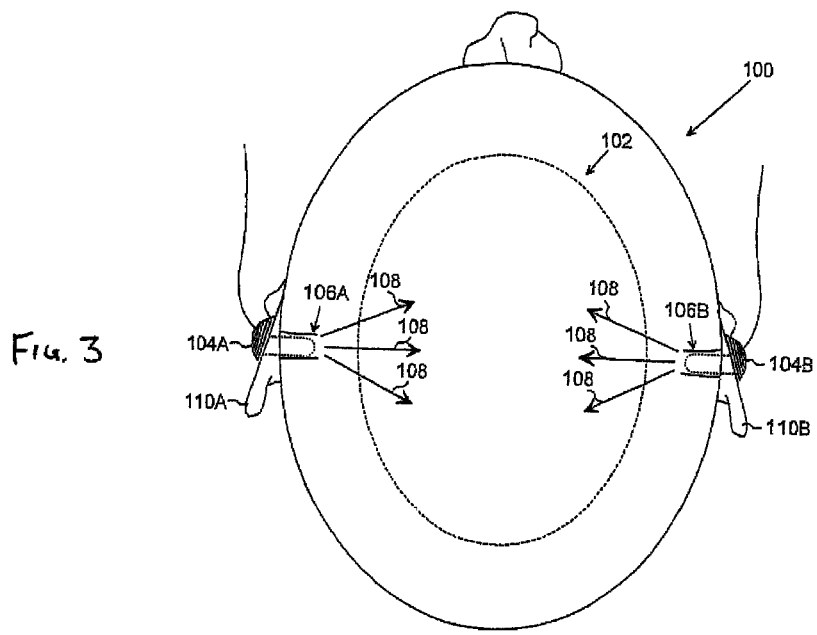
FIG. 3 illustrates a first example of an embodiment of a portable electronic device.
Figures 4, 5:
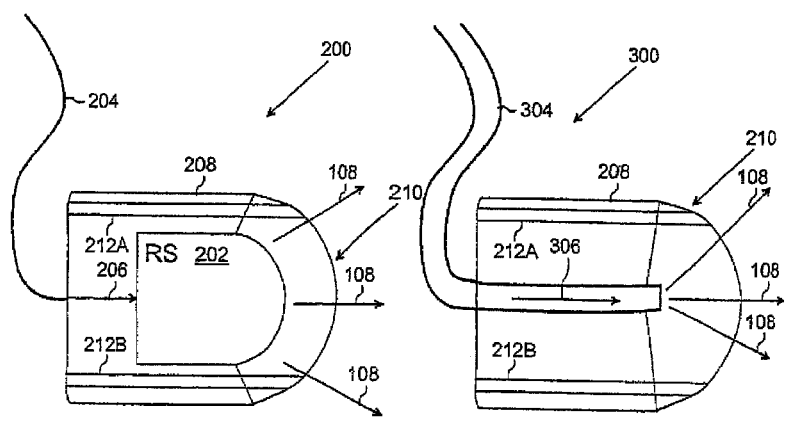
FIG. 4 illustrates a second example of an embodiment of a portable electronic device.
FIG. 5 illustrates a third example of an embodiment of a portable electronic device.

While the devices of FIGS. 3-5 are provided as examples, the description herein is agnostic as to the medical device used and does not presume the use of any particular device, whether or not described herein.

The qualities of the light delivered affect the spatial distribution of the light in the brain. According to the invention an intensity of 0.7-12 lumens, typically 1-10 lumens is used. In most cases 3-9 lumens is safe and sufficient for obtaining a clinical effect without adverse effects. In one embodiment an intensity of 4-9, or 6-9 lumens is used. With a light intensity of 1-12 lumens treatment times of 1-15, in most cases 6-12 minutes are suitable and adequate, e.g. 8-12 minutes treatment times are well applicable. The optimal optical radiation dose i.e. the light dose is 3-9 lumens for 6-12 minutes. According to one embodiment the light dose is 6-9 lumens for 8-12 minutes. Naturally a higher light intensity requires a shorter illumination time and vice versa.

The light used in the invention is bright light, which here refers to optical radiation that ranges in the visible spectrum from about 380 nm to about 780 nm, or in adjacent radiation regions of infrared and ultraviolet, which are not visible to the human eye. Typically the light is visible light, and especially light imitating natural sunlight. Illumination via the ear canal with light having a primary light spectrum peak in the blue region i.e. between 450 and 475 nm and a secondary in the green region i.e. between 495 and 570 nm is very effective. One such possible power distribution with a peak at about 465 nm and another at about 550 nm is presented in FIG. 1. The therapeutic effect can be induced by such a spectral power distribution as a whole, or its spectral power peaks, for example the 1.5E-04 W/nm peak at approximately 465 nm or 1.0E-04 W/nm peak at approximately 550 nm. The wave length distribution of optical radiation typically changes due to absorption in tissue.

The light therapy is conducted by providing the medical device described, applying the device to a subject in need of such therapy, and directing optical radiation with a light intensity of 0.7-12, typically 3-9 lumens non-invasively to the brain of the subject through an external auditory canal of the subject for 1-15, typically 6-12 minutes to stimulate the brain tissue of the subject.

The above described method of treatment by light therapy may be applied to any disorder or condition that is responsive to such treatment. The present invention especially provides a treatment alternative for a cluster of central nervous system (CNS) conditions, mood disorders, circadian rhythm sleep disorders and inflammatory diseases. CNS conditions as used herein and responsive to light therapy include but are not limited to: seasonal affective disorder (SAD), major depressive disorder (MDD), biopolar affective disorder, obsession compulsive disorder (OCD), migraine, post-traumatic stress, postpartum depression, Altzheimer's disease, Parkinson's disease, and anxiety. Circadian rhythm sleep disorder includes but is not limited to jetlag, shift work sleep disorder, and insomnia. Inflammatory diseases include but are not limited to autoimmune diseases like psoriasis, atopic skin, and skin disorders. Further premenstrual syndrome (PMS), and fertility disorders can be treated with light therapy. The light therapy is believed to optimize or increase dopamine levels in OCD and Parkinson, serotonin levels in e.g. mood disorders, chronic pain and migraine, and noradrenaline/norepinephrine levels in mood and neurological disorders.

Persons suffering from SAD are conveniently treated with the above described light therapy. Typically light having an intensity of 3-9 lumens is administered for 6-12 minutes at least once a day for at least five days a week during the season when SAD is symptomatic. SAD is considered as a sub-type of recurrent MDD, a sub-type of bipolar affective disorder in which depressive episodes regularly begin in one season and remit in another season, or as a sub-type of atypical depression characterized by mood reactivity and being able to experience improved mood in response to positive events. The winter-type of SAD manifests as atypical symptoms of depression that recur in the fall and winter, such as depressed mood, anhedonia, decreased activity, decreased libido, hyperphagia, hypersomnia, carbohydrate carving, fatigue and weight gain. It is believed possible that functional connectivity alterations related to SAD exist in brain regions earlier reported to involve metabolic changes in SAD patients. Epidemiological studies conclude that any population living above 30 degrees northern latitude, or below 30 degrees southern latitude have seasonal symptoms, and that in the US the prevalence correlates to the latitude.

People suffering from migraine constitute another group of patients that are responsive to the light therapy described. The typical migraine headache is unilateral pain (affecting one half of the head) and pulsating in nature, lasting from 4 to 72 hours; symptoms include nausea, vomiting, photophobia (increased sensitivity to light), phonophobia (increased sensitivity to sound), and is aggravated by routine activity. Approximately one-third of people who suffer from migraine headaches perceive an aura-unusual visual, olfactory, or other sensory experiences that are a sign that the migraine will soon occur. It is indeed remarkable that bright light administered intra-cranially via a non-ocular route can prevent migraine attacks or stop an already arousing migraine attack, because generally exposure to bright light via the eyes is considered as a major migraine-triggering factor. Typically light having an intensity of 3-9 lumens is administered for 6-12 minutes once a day to prevent migraine, or 1-6 times daily to relieve a migraine attack.

Usually light therapy treatment, using the light intensity and illumination times disclosed in the present invention, once a day is sufficient to achieve a clinical effect. This once-a-day treatment may be conducted for 1-3 or 1-5 days, or 1-4 or 1-6 weeks, or 1-3 or 1-6 months, or longer, or whenever needed depending on the disorder to be treated. Several daily doses, usually up to three daily doses, may be applied to treating an active migraine attack, fertility disorders, autoimmune diseases, Parkinson's disease, Altzheimer's disease, bipolar affective disease, OCD, or postpartum depression. Low light intensity, starting from 1 lumen may be used in treatments that continue for several weeks and/or for maintenance of a healthy condition.

The effect of the light therapy described may be monitored by analysing resting-state functional connectivity of the human brain. Spatial domain independent component analysis (ICA) may be applied to resting-state functional magnetic resonance imaging (fMRI) data in order to identify changes within the resting state networks (RSNs) that cover the entire cerebral cortex of the test persons. The entire brain cortex may be functionally segmented into a plurality of RSNs. Statistically significant increases in the functional brain connectivity of affected RSNs indicate the response to the light treatment. Changes in magnetic susceptibility correspond with changes in blood-oxygen-level (BOLD) contrasts in the region.

The invention is illustrated by the following non-limiting examples. It should be understood, however, that the embodiments given in the description above and in the examples are for illustrative purposes only, and that various changes and modifications are possible within the scope of the claims.

Example 1

Clinical Effect of Light Route and Dose

Different routes of light administration were briefly examined. Brain tissue of 10 subjects with SAD were illuminated via different delivery routes in a dark room and the eyes covered to avoid any ocular stimuli. Illumination was performed with highly targeted leds capable to administer bright light accurately (eye lid, ear, palate, temple) or an array of leds capable to administer bright light more broadly to the illuminated part of the head (palate, temple, back of the head). The response was measured with multiple physiological parameters such as EEG, heart rate, heart rate variation, body temperature and observable physiological changes. Subjects were also asked to evaluate their subjective response to treatment. The results are shown in Table 1.

TABLE 1

| Light administration | |
| --- | --- |
| Route | Result |
| Eye lid | No clinical efficacy comparable to ear route due to eye irritation. For clinical effect, intensity should exceed 3 lumens, which is already riskful for retina (2.7 lumen turned out to be threshold for pain). |
| Palate | No adverse events. Low observed clinical efficacy. Very inconvenient to use, and would cause lowered compliance to treatment. |
| Ear | High clinical efficacy. No adverse events. Easy to use. Auditory canal has the shortest distance to deep brain regions involved in most functions. |
| Below skull edge, at back of the head | No clinical efficacy. |
| Temple | No clear clinical efficacy; treatment focused onto frontal cortex and effects from midbrain, cerebellum, pons etc are not achieved. Non-optimal site to construct a device. |

Light administration via both ear canals using a device as disclosed in WO2008/29001 was chosen for further studies. The dosing study was done with 15 healthy volunteers and 5 SAD sufferers with a device capable of administering different time periods and intensities via the ear canal. Study subjects were lying awake in a silent and dark room with their eyes covered to block any external ocular or audio stimuli. The study was blinded for the subjects: They did not know if they were given bright light and with what parameters. Response to bright light after a daily treatment of maximum one week was assessed with structured interview and real-time monitoring of physiological stimuli such as heart rate, heart rate variation and EEG.

The results obtained with light intensities varying from 1 to 12 lumens, and duration of light exposure varying from 3 to >15 minutes are shown in Tables 2 and 3, respectively. The different light intensities were conducted for 6-12 minutes, and the different duration times were conducted with 3-9 lumens.

TABLE 2

| Light intensity in ear canal | |
| --- | --- |
| Intensity in ear canal | Result |
| 1 lumen | No or not measurable short-term clinical efficacy. |
| 3 lumens | No adverse events. Low observed clinical efficacy. Slight responses would need weeks use. |
| 4-6 lumens | High clinical efficacy. Immediate post-treatment subjective observations of psychotropic and cognitive responses. No adverse events. |
| 6-9 lumens | High clinical efficacy. Immediate post-treatment subjective observations of psychotropic and cognitive responses. Some subjects experience headache, dizziness, orthostatic hypotension or similar symptoms. |
| 12 lumens | Most subjects experience symptoms and feeling familiar with sunstroke, headache, dizziness or similar symptoms, orthostatic hypotension and even adverse effect on blood pressure, heat in the ear canal. |

TABLE 3

Light duration in ear canal

| Duration | Result |
|---|---|
| 3 min | No clinical efficacy |
| 6 min | No adverse events. First immediate experiences of alertness, "low dose" circadian entrainment and acute anxiolytic effect. Low observed clinical efficacy on severe mood disorders. |
| 8 min | High clinical efficacy. No adverse events. |
| 12 min | High clinical efficacy on severe mood disorders. Some patients experience headache and lightheadness. |
| 12-15 min | Many subjects experience symptoms and feeling familiar with sunstroke, headache, dizziness or similar symptoms, orthostatic hypotension, heat in the ear canal. |
| >15 min | Most subjects experience symptoms and feeling familiar with sunstroke, headache, dizziness or similar symptoms, orthostatic hypotension, heat in the ear canal, nausea and even vomiting. |

The optimal light dose in the above experiments was 3-9 lumens for 6-12 minutes.

Dose response for SAD was further studied in a 3-arm dose response trial, where patients were divided into 0.7 lumen, 4 lumen and 9 lumen light intensity groups. Each group had 30 patients. Each patient was given a respective device to use once a day for 6-12 minutes for 4 weeks at home. The patients were evaluated by a qualified psychiatrist for their level of seasonal depression with Structural Interview Guide for the Hamilton Depression Rating Scale SIGH-SAD at the beginning and at the end of study, and they completed BDI21 self-rating scale weekly at home. The results indicated that up to approximately 80% had symptoms significantly decreasing in each study group. The patients in the 9 lumen and 4 lumen groups remitted significantly faster, typically in 1 to 3 weeks, compared to the 0.7 lumen group who remitted in 4 weeks.

Example 2

Clinical Trial with SAD Patients

The optimal dose was later selected into a clinical trial with 13 SAD patients. A pilot prospective study on the putative effect of intra-cranial bright light in the treatment of winter SAD was run.

The light was produced by using phosphor-based white led (465 nm blue light led basis) with a secondary light spectrum peak at 550 nm in a main unit by two 3 W power-LEDs, which is a medical device approved in the European Union. The amount of photic energy was 6.0-8.5 lumens in both ear canals, and the length of treatment was 8 to 12 minutes five times a week during a four-week study period. The patients did not receive any other treatments during the study period.

Subjects were recruited through advertisements in the city of Oulu, Finland (latitude 65° 01'N). The final patient series consisted of 13 (aged 37.1±7.2 years) physically healthy indoor workers suffering from major depressive disorder with seasonal pattern according to DSM-IV-TR criteria. Severity of depressive symptoms was assessed using the HAM D-17 and BDI-21. The ethical committee of Oulu University Hospital approved the study protocol.

Figure 2:
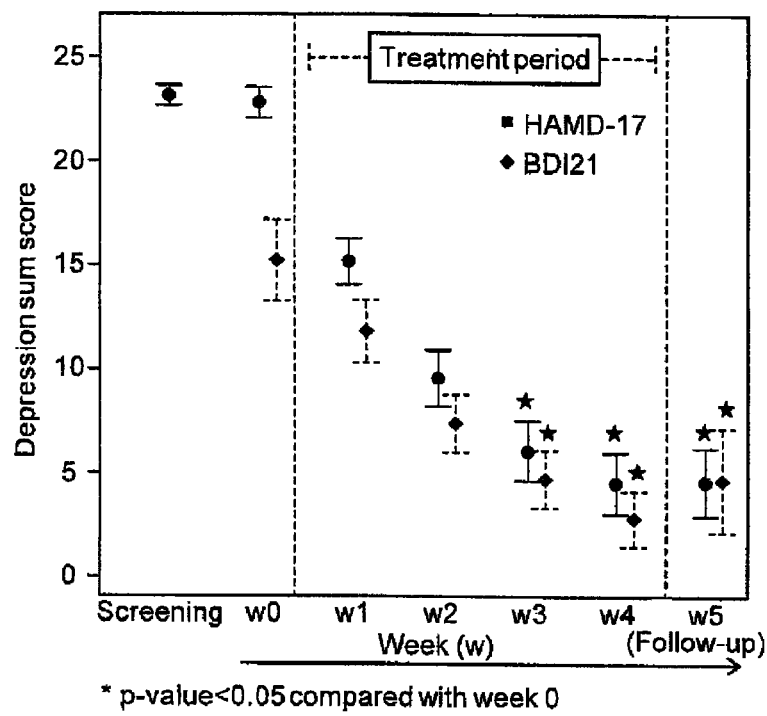
FIG. 2 shows Hamilton Depression Scale (HAMD-17) and Beck Depression Inventory (BDI-21) scores in human subjects treated by intra-cranial brain-targeted bright light via the ear canals. Data is expressed as mean±SEM. Overall treatment effect: HAMD-17, $p<0.001$ and BDI-21, $p<0.001$.

The HAMD-17 mean sum score at screening was 23.1±1.6. Ten out of 13 SAD patients (76.9%) achieved full remission (i.e., HAMD-17 sum score 7), and 92.3% (12/13) at least 50% reduction in HAMD-17 sum scores at "Week 4". By using a mixed regression model of repeated measures (AR-1) controlling for age, gender, HAMD-17 mean sum score at screening, significant differences were found comparing the HAMD-17 mean sum scores of "Week 0" with the corresponding scores at the "Week 3" (t=−2.05, p=0.045) and "Week 4" visits (t=−2.77, p=0.008) (FIG. 2). Correspondingly, significant differences were found comparing (age and gender controlled) the BDI-21 mean sum scores (15.2±6.7) of "Week 0" with the corresponding scores at the "Week 3" (t=−2.37, p=0.021) and "Week 4" visits (t=−3.65, p<0.001). The results are also shown in FIG. 2.

Example 3 fMRI Analysis of the Brain of SAD Patients During Light Therapy fMRI research was conducted to show modulation of the human brain caused by light treatment with the selected, optimal light dose. For provision of reference information applicable in detection of SAD, fMRI was used to collect test data from 45 medication-free subjects with SAD, and 45 age-, gender- (39.78±10.64, 30 ♀, 15 ♂) and ethnicity-matched healthy control subjects (no concomitant medications) from the general population. The test groups were imaged with fMRI using the same test protocol during one winter-period. All subjects with SAD were scanned within one week after they were diagnosed.

During measurements, resting-state BOLD data were collected on a whole body fMRI system with an eight channel receive coil, using a defined sequence (EPI GRE sequence: TR 1800 ms, TE 40 ms, 280 time points, 28 oblique axial slices, slice thickness 4 mm, inter-slice space 0.4, whole brain coverage, FOV 25.6 cm×25.6 cm, with 64×64 matrix, parallel imaging factor 2, flip angle 90°). T1-weighted scans were imaged using 3D FSPGR BRAVO sequence (TR 12.1 ms, TE 5.2 ms, slice thickness 1.0 mm, FOV 24.0 cm, ma-trix 256× 256, and flip angle 20°, and NEX 1) in order to obtain anatomical images for co-registration of the fMRI data to standard space coordinates. For resting state, the subjects were instructed to simply lay still inside the scanner with their eyes closed, think of nothing particular and not to fall asleep. Motion was minimized using soft pads.

ICA was used as a data-driven analysis tool for processing fMRI-generated voxel values. It was shown that by increasing the number of ICA estimated sources, one can probe the entire brain cortex with finely detailed sub-networks. ICA allows differentiating relevant functional brain signals from various sources of noise without a priori knowledge of the signal origin. It also separates noise sources from detected data and then provides spatial maps of functionally independent brain networks.

In the exemplary tests the results revealed that SAD patients compared to age-, gender- and ethnicity-matched healthy control subjects showed statistically significant increases in functional connectivity involving several RSNs. SAD-related increased functional connectivity was shown at two different functional levels while mainly focusing on the detailed RSNs level (70 ICs). Large-scale functional brain networks were localized using low model order ICA of 20 components. Significant increases in functional connectivity were detected in 4 out of 11 identified RSNs in patients with SAD. Segmentation of the brain functionality into detailed sub-networks using a high model order ICA of 70 components yielded 47 RSNs. Significant increases in functional connectivity were detected in 25 RSNs out of the 47 identified networks. Datasets of spatial maps on the detected RNSs and/or of the RNSs of altered functional connectivity are thus applicable as reference information related to a defined physiological disorder, in this example SAD.

Example 4

Light Therapy Effect on Migraine

The treatment modality tested was as follows for (a) preventive and (b) attack treatment:
(a) Preventive Treatment
 One daily dose
 6-12 minutes
 3-10 lumens intra-cranial via non-ocular route via each ear canal with a light source in each ear
 Visible light spectrum imitating natural sunlight
 Administered during the day at the time resulting into best patient-evaluated treatment response The most typical feedback was that a daily dose kept the attacks away completely.

Examples of patient feedback for the above mentioned use is given below:

P1 started the light therapy in spring 2010, and almost completely got rid of her migraine attacks. After being without light therapy for a couple of months, the attacks returned. The light treatment functioned as a preventive medicine, but does not cure the attack. Regularly used it prevents the attacks or at least alleviates them.

P2 found that the light treatment kept the migraine attacks away. After no light therapy for five days, the attacks returned.

P3 who was suffering from repeated migraine attacks did not have any attack during the light treatment period.
(b) Migraine Attack in Progress-Treatment
 One to three doses as described in the preventive treatment when the migraine attack is arising or at its full, at intervals depending on individual progression of the migraine attack.

The most typical feedback is that one to three doses when the attack is arousing or in progress aborts the attack or delays it.

Examples of patient feedback for the above mentioned use is given below:

P4 found that he could postpone the migraine attack when he conducted the light therapy in the beginning of the attack.

P5 took medication during a migraine attack, and further conducted light therapy. She found that the light therapy improved the pain-relieving effect during the attack.

P6 found that the light therapy relieved an on-going attack.

Example 5

Light Treatment of Jet Lag

In jet lag, the body clock is out of synchronization as it experiences daylight and darkness contrary to the rhythms to which it has grown accustomed to. A number of volunteers tried the light-emitting ear plugs described in WO2008/29001 with a light intensity of 3-9 lumens for 8-12 minutes at about the desired wake-up time at the destination. The feedback has been very positive. Here are two examples:

P7 conducted the light treatment for 8 minutes, 1.5 hours after the desired wake-up time for one week at a destination with 9 hours time difference from the departure. From the very first day onwards she fell no jetlag symptoms, that she usually has, especially the afternoon-dizziness was missing. She continued with the light treatment when back home, and the results were as good. There were no problems this time to get back to the rhythm.

P8 used the same light treatment when travelling from Europe to the American west coast. He did not experience jetlag, and his colleagues were wondering why he was not feeling tired during afternoon meetings.

Example 6

Treatment Modalities

The following treatment modalities using intra-cranial administration of bright light via the ear canals with two led lights into two ears with 3-9 lumens (lm) intensity for 6-12 minutes were found effective:

1. once a day for SAD during the season or episode when the disorder is symptomatic;
2. once a day for PMS during the menstrual cycle, or up to five days prior to menstruation, or when individual symptoms start to occur;
3. once a day for migraine as preventive treatment;
4. one to several doses daily when treating migraine seizure/attack;
5. once a day at the desired wake-up time at destination for jet lag or desired alertness time shift work;
6. once a day for post-traumatic stress disorder;
7. once a day for MDD;
8. one to three times a day for OCD;
9. One dose (might be repeated when necessary) for acute treatment in anxiety or anxiety disorder (AD);
10. Once or more times a day to treat acute or chronic inflammation;
11. +1-(−2) h from desired wakeup-time for shift work sleep disorder. If entrainment this way causes too early wakeup, then on the "desired noon". All wavelength with blue spectra and short wavelengths emphasized.

Even lower light intensities may be used for the following indications:

| Indication | Intensity | Timing | Light Properties |
|---|---|---|---|
| Fertility | 1-9 lm | 1-3 times daily at daytime Light/Dark-ratio enhancement enabled with 2 or more sessions. | All wave-lengths, blue spectra allows smaller intensity in the evening. |
| Autoimmune: psoriasis, atopic skin, skin disorders | 1-9 lm | 1-3 times daily at daytime | All wave-lengths with green spectra emphasized. |
| Alzheimer | 1-9 lm | 1 or more times daily, treatment total energy according to disease severeness. | All wave-lengths with green and infrared emphasized. |

-continued

| Indication | Intensity | Timing | Light Properties |
|---|---|---|---|
| Bipolar affective disease | 1-9 lm | 1-3 times daily. Morning dose carefully timed according to mood response. | All wave-lengths |
| Postpartum depression | 1-9 lm | 1-3 times daily at daytime | All wave-lengths |
| Anxiety | 1-9 lm | High intensity (4-9 lm) on acute symptoms, lower (1-6 lm) for maintenance. | All wave-lengths |
| Optimizing/increasing dopamine levels in OCD and Parkinson's | 1-12 lm | From 1 (with large intensities) to several (with smaller intensities) times daily. 2 doses (morning + evening) with 3-6 lm threshold to markedly activate substantia nigra and enhance dopamine action in brain. | All wave-lengths |
| Optimizing/increasing 5-HT (serotonin) levels in mood disorders, chronic pain, migraine and other diseases | 1-12 lm | 1-3 times daily. Increased raphe nuclei activity and enhanced monoamine metabolism causing increased 5-HT level also elsewhere in brain. | All wave-lengths |
| Optimizing/increasing noradrenaline/norepinephrine levels in mood and neurological disorders | 1-9 lm | 1-3 times daily, increased locus caerulus activity. | All wave-lengths |
| Insomnia, difficulty in falling asleep | 1-4 lm or 5-9 lm | Shorter treatment periods with 5-9 lm (1-4 lm/4-12 min, 5-9 lm/1-4 min). 3-0 hrs before bedtime, alternatively morning/daytime use with high doses. | All wave-lengths, blue spectra should be diluted on higher intensities to avoid entrainment if evening dose used. |

The invention claimed is:

1. A method of treating a subject in need of light therapy, said method comprising
providing a medical device, comprising an optical radiation source and a light guide, for directing light directly into the ear canal of the subject,
directing non-invasively, intra-cranially via both of the subject's ear canals bright light having an intensity of 6.0-8.5 lumens for a treatment time of 8-12 minutes once a day for at least five times a week for at least three weeks, with the bright light having a primary light spectrum peak in the blue region; and
reducing depressive symptoms of the subject via direction of light directly into the ear canals of the subject.

2. The method of claim 1, wherein the bright light has a secondary light spectrum peak in the green region.

3. The method of claim 1, wherein the bright light is directed using at least one light-emitting ear plug which at least partially penetrates into the ear canal.

4. The method of claim 1, including the step of showing, via functional magnetic resonance imaging (fMRI) testing, SAD-related increased functional connectivity in the subject's brain after the step of treating a subject suffering from SAD has commenced.

5. The method of claim 1, wherein the bright light has a primary light spectrum peak between 450 and 475 nm.

6. The method of claim 2, wherein the bright light has a secondary light spectrum peak between 495 and 570 nm.

7. The method of claim 1, wherein the step of reducing depressive symptoms of the subject via direction of light directly into the ear canal of the subject includes treating a subject suffering from at least one of seasonal affective disorder (SAD), major depressive disorder (MDD), bipolar affective disorder, and atypical depression.

8. The method of claim 7, including the step of treating a subject suffering from SAD during the season when SAD is symptomatic.

9. The method of claim 7, including the step of showing, via functional magnetic resonance imaging (fMRI) testing, SAD-related increased functional connectivity in the subject's brain after the step of treating a subject suffering from SAD has commenced.

* * * * *